(12) United States Patent
Popoola et al.

(10) Patent No.: US 9,248,020 B2
(45) Date of Patent: Feb. 2, 2016

(54) CERAMIC MONOBLOCK IMPLANTS WITH OSSEOINTEGRATION FIXATION SURFACES

(75) Inventors: Oludele O. Popoola, Granger, IN (US);
David M. Miller, Warsaw, IN (US);
Jeffrey P. Anderson, Warsaw, IN (US);
Brian H. Thomas, Lakeland, FL (US)

(73) Assignee: Zimmer, Inc., Warsaw, IN (US)

( * ) Notice: Subject to any disclaimer, the term of this patent is extended or adjusted under 35 U.S.C. 154(b) by 221 days.

(21) Appl. No.: 13/885,918

(22) PCT Filed: Nov. 16, 2011

(86) PCT No.: PCT/US2011/060973
§ 371 (c)(1),
(2), (4) Date: Sep. 20, 2013

(87) PCT Pub. No.: WO2012/068239
PCT Pub. Date: May 24, 2012

(65) Prior Publication Data
US 2014/0005796 A1 Jan. 2, 2014

Related U.S. Application Data

(60) Provisional application No. 61/414,729, filed on Nov. 17, 2010.

(51) Int. Cl.
*A61F 2/28* (2006.01)
*A61L 27/06* (2006.01)
(Continued)

(52) U.S. Cl.
CPC . *A61F 2/28* (2013.01); *A61L 27/06* (2013.01); *A61L 27/10* (2013.01); *A61L 27/306* (2013.01)

(58) Field of Classification Search
CPC ......... A61F 2/28; A61F 2/30; A61F 2/30723; A61F 2/30724; A61F 2/30756; A61F 2/34; A61F 2002/28; A61F 2002/2817; A61F 2002/2835; A61F 2002/2839; A61F 2002/30; A61F 2002/34; A61L 27/06; A61L 27/10; A61L 27/306; A61L 27/56; A61L 27/28; A61L 27/40; A61L 31/02; A61L 31/026; A61L 31/028; A61L 31/146; A61L 2300/608; A61L 2420/08
USPC .......................................... 623/23.53–23.57
See application file for complete search history.

(56) References Cited

U.S. PATENT DOCUMENTS 5,030,396 A * 7/1991 Saita et al. .................... 264/610
5,702,474 A * 12/1997 McCandliss ....... A61B 17/7098
623/13.12

(Continued)

FOREIGN PATENT DOCUMENTS

WO WO-2009103775 A2 8/2009
WO WO-2012068239 A1 5/2012

OTHER PUBLICATIONS

"European Application Serial No. 09774115.1, Communication pursuant to Rules 161 (1) and 162 EPC mailed Jul. 26, 2013", 2 pgs.

(Continued)

*Primary Examiner* — Alvin Stewart
(74) *Attorney, Agent, or Firm* — Schwegman Lundberg & Woessner, P.A.

(57) ABSTRACT

Monoblock orthopedic and/or dental implants are disclosed. The monoblock implants include a ceramic articulating surface and an osseointegrative bone-contacting surface. Methods of making such implants also disclosed.

10 Claims, 8 Drawing Sheets

(51) Int. Cl.
*A61L 27/10* (2006.01)
*A61L 27/30* (2006.01)

(56) References Cited

U.S. PATENT DOCUMENTS

| | | | | |
|---|---|---|---|---|
| 6,139,585 A * | 10/2000 | Li | | 623/23.57 |
| 6,171,310 B1 * | 1/2001 | Giordano | | A61F 2/0805 606/53 |
| 6,447,550 B1 * | 9/2002 | Hunter | | C23C 8/10 623/22.15 |
| 6,626,950 B2 * | 9/2003 | Brown | | B29C 44/1214 623/23.72 |
| 6,719,987 B2 * | 4/2004 | Burrell et al. | | 424/405 |
| 6,833,197 B1 * | 12/2004 | Dong | | C23C 8/80 148/237 |
| 6,858,042 B2 * | 2/2005 | Nadler | | A61F 2/28 424/423 |
| 6,869,701 B1 * | 3/2005 | Aita | | A61L 27/306 428/336 |
| 7,473,278 B2 * | 1/2009 | Hunter | | A61L 27/306 623/23.39 |
| 7,578,851 B2 * | 8/2009 | Dong | | C23C 28/028 623/22.21 |
| 7,771,483 B2 * | 8/2010 | Justin | | A61B 17/157 623/20.34 |
| 7,867,280 B2 * | 1/2011 | Goble | | A61B 17/157 606/304 |
| 7,896,926 B2 * | 3/2011 | Hunter | | A61L 27/306 623/22.4 |
| 8,012,205 B2 * | 9/2011 | Plouhar et al. | | 623/13.17 |
| 8,399,008 B2 * | 3/2013 | Webster et al. | | 424/423 |
| 8,415,019 B2 * | 4/2013 | Pawar | | A61F 2/30767 428/469 |
| 8,556,972 B2 * | 10/2013 | Gordon | | A61F 2/30756 623/16.11 |
| 8,556,981 B2 * | 10/2013 | Jones | | B23K 26/382 623/18.11 |
| 8,556,987 B2 * | 10/2013 | Hunter | | A61L 27/306 623/23.56 |
| 8,862,258 B2 * | 10/2014 | Nimal | | 700/98 |
| 9,011,965 B2 * | 4/2015 | Gan | | A61L 27/30 427/2.26 |
| 2001/0039455 A1 * | 11/2001 | Simon | | A61B 17/1604 623/23.51 |
| 2002/0018798 A1 * | 2/2002 | Sewing et al. | | 424/423 |
| 2002/0107520 A1 * | 8/2002 | Hoffman | | A61B 17/15 623/23.11 |
| 2003/0099762 A1 * | 5/2003 | Zhang | | A61L 27/30 427/2.1 |
| 2003/0114936 A1 * | 6/2003 | Sherwood | | A61F 2/28 623/23.58 |
| 2003/0153981 A1 * | 8/2003 | Wang | | A61F 2/30767 623/22.21 |
| 2004/0122524 A1 * | 6/2004 | Hunter | | A61F 2/30767 623/22.18 |
| 2004/0153165 A1 * | 8/2004 | Li et al. | | 623/23.57 |
| 2006/0210494 A1 * | 9/2006 | Rabiei | | A61C 8/0012 424/57 |
| 2007/0113951 A1 * | 5/2007 | Huang | | A61F 2/30756 156/89.11 |
| 2007/0118243 A1 * | 5/2007 | Schroeder et al. | | 700/118 |
| 2007/0150068 A1 * | 6/2007 | Dong et al. | | 623/22.32 |
| 2007/0181239 A1 * | 8/2007 | Yamazawa et al. | | 156/62.2 |
| 2007/0184299 A1 * | 8/2007 | Wei | | A61L 27/306 428/689 |
| 2007/0287027 A1 * | 12/2007 | Justin et al. | | 428/666 |
| 2009/0192610 A1 * | 7/2009 | Case et al. | | 623/16.11 |
| 2009/0226668 A1 * | 9/2009 | Simon | | 428/143 |
| 2010/0137990 A1 * | 6/2010 | Apatsidis et al. | | 623/17.16 |
| 2010/0174377 A1 * | 7/2010 | Heuer | | 623/20.14 |
| 2010/0174383 A1 * | 7/2010 | Pawar | | A61F 2/30767 623/23.56 |
| 2010/0178312 A1 * | 7/2010 | Webster et al. | | 424/423 |
| 2010/0268337 A1 * | 10/2010 | Gordon | | A61F 2/30756 623/16.11 |
| 2010/0310623 A1 * | 12/2010 | Laurencin et al. | | 424/423 |
| 2010/0318108 A1 * | 12/2010 | Datta et al. | | 606/151 |
| 2010/0331979 A1 * | 12/2010 | McDade et al. | | 623/14.12 |
| 2010/0331998 A1 * | 12/2010 | Ringeisen | | 623/23.61 |
| 2011/0003083 A1 * | 1/2011 | Yang | | A61F 2/30767 427/453 |
| 2011/0014258 A1 * | 1/2011 | Gan | | A61L 27/30 424/409 |
| 2011/0143127 A1 * | 6/2011 | Gupta | | A61L 27/30 428/336 |
| 2011/0251698 A1 * | 10/2011 | Gupta | | A61F 2/30767 623/23.56 |
| 2012/0253474 A1 * | 10/2012 | Klein et al. | | 623/23.76 |
| 2013/0001090 A1 * | 1/2013 | Rubinson et al. | | 205/118 |
| 2013/0053938 A1 * | 2/2013 | Miller et al. | | 623/1.1 |
| 2013/0189606 A1 * | 7/2013 | Ruettinger | | H01M 4/8605 429/508 |
| 2013/0190888 A1 * | 7/2013 | Novak Krmpotic et al. | | 623/23.6 |
| 2013/0190889 A1 * | 7/2013 | Li | | A61F 2/34 623/23.11 |
| 2013/0310948 A1 * | 11/2013 | Luscher | | 623/23.58 |
| 2014/0005796 A1 * | 1/2014 | Popoola | | A61L 27/06 623/23.51 |
| 2014/0018931 A1 * | 1/2014 | Gillard et al. | | 623/21.18 |
| 2014/0277530 A1 * | 9/2014 | Stalcup | | A61F 2/30749 623/20.17 |
| 2014/0308628 A1 * | 10/2014 | Carrad | | A61L 27/32 433/173 |
| 2015/0004042 A1 * | 1/2015 | Nimal | | 419/2 |
| 2015/0110846 A1 * | 4/2015 | Yu et al. | | 424/423 |

OTHER PUBLICATIONS

"International Application Serial No. PCT/US2011/060973, International Preliminary Report on Patentability mailed May 30, 2013", 8 pgs.

"International Application Serial No. PCT/US2011/060973, International Search Report mailed Feb. 16, 2012", 4 pgs.

"International Application Serial No. PCT/US2011/060973, Written Opinion mailed Feb. 16, 2012", 8 pgs.

Barth, E., et al., "Bioactive glass ceramic on titanium substrate: The effect of molybdenum as an intermediate bond coating", Biomaterials, Elsevier Science Publishers BV vol. 7 No. 4, (Jul. 1, 1986), 273-276 pgs.

* cited by examiner

CERAMIC MONOBLOCK IMPLANTS WITH OSSEOINTEGRATION FIXATION SURFACES

CROSS-REFERENCE TO RELATED APPLICATION

This application is a U.S. National Stage Filing under 35 U.S.C. 371 of International Patent Application Serial No. PCT/US2011/060973, filed on Nov. 16, 2011, published on May 24, 2012 as WO 2012/068239 A1, which claims the benefit of priority under 35 U.S.C. 119(e) of U.S. Provisional Patent Application Ser. No. 61/414,729 filed on Nov. 17, 2010, the benefit of priority of each of which is claimed hereby and the entire contents of each of which are incorporated herein by reference in its entirety.

FIELD OF THE DISCLOSURE

The present disclosure generally relates to monoblock orthopedic implants having bone-contacting surfaces adapted to allow for and promote bone ingrowth. More particularly, the present disclosure relates to monoblock implants made substantially of a ceramic material and including one or more bone-contacting surfaces that have been modified to allow for bone ingrowth. The present disclosure also relates to methods for making such implants.

BACKGROUND

Orthopedic implants are commonly used to replace some or all of a patient's joint such as a hip, knee, shoulder or elbow where deterioration of or damage to the joint has occurred due to aging, illness, injury or trauma. Orthopedic implants are commonly made of metal, ceramic, polymeric materials, or some combination thereof. For example, orthopedic implants commonly include a metal or ceramic portion that articulates against a polymeric bearing surface, or a metal surface that articulates against a facing metal or ceramic surface. In a hip replacement, the orthopedic hip implant will typically include a femoral component having a metallic or ceramic head that articulates against a polymeric (or metal or ceramic) surface of an acetabular cup. The polymeric bearing surface of the acetabular cup is typically contained within a metal or metal-containing shell which has been treated, formed, or otherwise adapted to allow for and promote bone ingrowth. The metal or metal-containing shell may incorporate, at its outer or bone contacting surface, porous titanium, tantalum, or a tantalum foam, such as Trabecular Metal™, a material used in orthopedic implants made by Zimmer, Inc., of Warsaw, Ind., and discussed in greater detail below.

In general, implants are classified as either modular or monoblock (i.e., single piece). Modular orthopedic implants are those where the implant is composed of two or more assembled parts connected by a locking mechanism and allowing for some of the constituent parts to be replaceable. For example, in a modular acetabular cup, the polymeric portion (that includes the bearing surface) is attached by mechanical means to the inside of a metal shell. With this arrangement, surgeons can replace a defective polymeric insert with another polymeric, ceramic or metal insert without disrupting the fixation of the shell to the bone. In contrast, monoblock implants are considered "single-piece" implants where the constituent components are integral and not interchangeable.

With respect to the interaction between articulating surfaces, a common concern is the generation of debris resulting from the relative motion of such surfaces. For example, motion between a metal component and a polymeric material, or the motion between facing metal surfaces may result in the release of polymeric or metallic debris into the surrounding environment. Such debris can interfere with the proper function of the orthopedic implant as well as cause an undesirable autoimmune response in the patient. For these reasons, research and development of low friction orthopedic implants that minimize the generation of debris is ongoing.

In addition to minimizing the friction between articulating surfaces and thereby limiting the production of debris, secure affixation of the implant within the bone is an extremely important aspect of joint replacement. Long-term stabilization of the implant is often achieved by incorporation or integration of the implant into the surrounding natural bone of the patient. Over time, bone from the surrounding tissue will grow into and around the implant and secure the implant to the bone tissue. This phenomenon is often referred to as osseointegration. To promote osseointegration, orthopedic implants are commonly provided with a bone-contacting surface that allows and promotes bone ingrowth. For example, many implants are provided with a porous bone-contacting surface which allows bone tissue to extend and grow into the pores of such surface. Examples of such implants are those that include a porous metal surface, such as titanium or tantalum, and implants including the previously mentioned Trabecular Metal™.

As noted above, in addition to the metal and polymeric materials used in many of the currently available implants, other materials such as ceramics have likewise been used in orthopedic implants, particularly modular implants. Ceramic materials and implants including ceramic articulating surfaces are believed to reduce the amount of debris generated by the motion of the articulating surfaces. One example of a ceramic implant is disclosed in U.S. Pat. No. 7,695,521, the contents of which are incorporated herein by reference. Another example of a ceramic-based implant is disclosed in WO 2009/103775 A2, the contents of which are also incorporated herein by reference. Ceramic materials for use with orthopedic implants and/or dental implants are described in U.S. Pat. No. 6,534,197, the contents of which are likewise incorporated herein by reference. While the use of ceramic materials in a modular implant, where the ceramic portion that includes the bearing surface is mechanically attached to a component that includes metal is known, monoblock implants (wherein the ceramic component is bonded to or otherwise attached without mechanical locking mechanisms) with an integral bone in-growth surface have been more difficult to achieve.

Accordingly, it would be desirable to provide a ceramic monoblock implant wherein the bone-contacting surface allows for a reliable and secure affixation through osseointegration with natural bone.

SUMMARY

In one aspect, the present disclosure is directed to a monoblock orthopedic implant, including a ceramic substrate having an inner bearing surface and a treated outer surface. The monoblock implant includes a metallic scaffold adapted for osseointegration that is bonded to the treated outer surface of the substrate.

In another aspect, the present disclosure is directed to a method of making a monoblock implant having a ceramic bearing surface or a ceramic articulating surface and a treated outer surface adapted for osseointegration of the implant with natural bone. The method includes providing a ceramic substrate and treating the substrate to provide an oxygen rich surface. A least one layer of metal is then deposited onto the oxygen rich surface so as to provide a modified outer surface. In a further step, an osseointegrative scaffold is then bonded to the modified surface of the ceramic monoblock implant.

The present disclosure generally relates to monoblock orthopedic implants that include articulating or bearing surfaces made of non-polymeric, non-metallic materials such as low friction ceramic materials. Monoblock orthopedic implants of the type disclosed herein also include an integral bone-contacting surface that allows for bone ingrowth, i.e., osseointegration.

In one embodiment, the implant includes at least an articulating or bearing surface made of a non-metallic, non-polymeric material such as ceramic. Indeed, in an exemplary embodiment, implants of the type disclosed herein are made substantially of ceramic. In accordance with the present disclosure, although the monoblock implant is made substantially of ceramic, the portion of the implant that interfaces and is attached to the bone, i.e., the bone-contacting surface is modified to provide a surface that allows for and promotes bone ingrowth.

As noted above, implants of the present disclosure are monoblock implants in that they are comprised of two or more different portions or constituent parts bonded together to provide an integral implant. As such, substantially ceramic monoblock implants are distinguished from modular implants that include ceramic components in that the components are not separable and do not utilize locking mechanisms (as is common in modular implants) to attach or assemble together the separable components of the implant. Thus, monoblock implants of the present disclosure avoid some of the potential drawbacks associated with modular implants such as reliability of the locking mechanisms and the possible introduction of unwanted debris which may contribute to implant failure and autoimmune responses in the patient.

In accordance with the present invention, the inner bearing surface may be made of a low-friction, non-metallic, non-polymeric material. Preferably, the articulating surface is made of a ceramic material that is suitable for use in biomedical applications. More typically, the implant comprises a ceramic substrate made substantially or even entirely of the low friction, non-metallic, non-polymeric material, such as ceramic with a selected surface of the ceramic substrate modified to provide the bone-contacting layer as described in detail below.

The ceramic material selected is preferably suitable and approved for human use, i.e., biocompatible. Preferably, the ceramic material is likewise corrosion resistant, substantially wear resistant, and has a low coefficient of friction. The ceramic material should also have good mechanical strength. Examples of suitable ceramic materials include, but are not limited to, aluminum oxide, zirconium oxide, silicon nitride, zirconia-toughened alumina (ZTA) and alumina-toughened zirconia (ATZ).

The implant includes an outer surface that has been adapted to allow for and promote osseointegration of the implant with the natural bone of the patient. The outer surface preferably includes a porous metallic material selected to allow for and promote bone growth. Suitable materials include certain metallic materials based on, for example, titanium and tantalum. Certain metals or metal-containing materials are sufficiently porous or can be deposited in a way that creates a porous surface that allows for bone ingrowth. In a preferred embodiment, the metallic materials that can be used to provide the osseointegrative surface of the implant include metallic foams, such as titanium foam, tantalum foam, or stainless steel foam.

One example of suitable metallic foam is Trabecular Metal™. Trabecular Metal™ is a material used in orthopedic implants made by Zimmer, Inc., of Warsaw, Ind., and is described in, for example, U.S. Pat. No. 5,282,861, which is incorporated herein by reference. Trabecular Metal™ approximates the physical and mechanical properties of natural bone. It is highly porous and conducive to bone growth. Trabecular Metal™ has good corrosion resistance and is, of course, biocompatible. Trabecular Metal™ is formed by coating the surface of a pre-formed carbon foam with tantalum metal by, for example, chemical vapor deposition (CVD).

The present disclosure is directed to a method of making a monoblock implant having a ceramic bearing surface or a ceramic articulating surface and a treated outer surface adapted for osseointegration of the implant with natural bone. In the method, a ceramic substrate is provided. The ceramic substrate may be pre-formed in the shape of the desired orthopedic implant. The substrate or pre-form may be made substantially of a ceramic material, such as aluminum oxide, zirconium oxide, or silicon nitride.

The bone interfacing surface of the ceramic pre-form is preferably activated to provide a surface for bonding materials adapted for osseointegration, as well as for intermediate coatings, layers and depositions that allow for integral attachment of the bone ingrowth promoting material to the ceramic substrate. For example the outer surface may be activated or otherwise treated to provide an oxygen rich surface. Inasmuch as ceramic by itself does not provide the desired osseointegrative and attachment properties, treating or activating the ceramic outer surface to provide an oxygen-rich surface allows for subsequent bonding of the osseointegrative materials described below.

The oxygen rich surface may be provided in several different ways. For example, an oxygen rich outer surface may be provided by subjecting the ceramic surface to oxygen plasma etching or multiple energy oxygen ion implantation. Ion beam implantation is a process that changes the physical and electronic properties of a material by forcibly embedding different types of ions onto the material. In general, the ion implanter includes an ionization chamber where ions are created and an accelerator where they are boosted up to speeds high enough to penetrate the target material to the desired depth for example with an applying energy of approximately 200-800 KeV.

Once the ceramic surface has been treated to provide an oxygen rich activated surface, such activated surface may be further treated by depositing one or more metallic materials onto the surface. The deposited metallic materials (which can be provided as a paint, coating or sheet metal) are selected such that the metal firmly bonds to the activated oxygen rich surface of the ceramic pre-form and likewise bonds to a final osseointegrative, i.e., bone-contacting surface of the implant. For example, where the osseointegrative bone-contacting surface includes the previously described metallic foams, materials that may bond to such foams and the ceramic substrate include titanium, titanium-aluminum-vanadium or zirconium, and/or alloys of one or more of the above.

The activated ceramic surface is preferably treated with multiple layers or depositions of a metal or metallic-based material. The multiple materials may include three deposited layers or coatings of selected metallic materials. The layers or coatings may be titanium layers, while an intermediate layer may be any material that can serve as a thermal expansion compensator, which is described in greater detail below. Typically, the layers are applied sequentially and the combined multi-layered construct may have a thickness of typically between 3-5 μm and up to about 1 mm. Of course, the thickness of the multi-layered construct will depend, in part, on the type and size of implant. The layers may be applied by a variety of techniques including, but not limited to, electron beam evaporation, sputter deposition, plasma spray, spray painting of dispersed powder suspensions, and other comparable processes that will be known to those of skill in the art.

The ceramic substrate may be further modified to include an outer bone-contacting, osseointegrative surface. The outer bone-contacting surface may be provided as a pre-formed scaffold that is attached to the modified surface. The scaffold may be provided in any shape that conforms to the desired surface of the selected implant component. The scaffold may be made by casting. Alternatively, scaffold may be made by providing a carbon foam in a predetermined shape and depositing the desired (metal) material onto the foam. In yet another alternative, the scaffold may be made by bubbling gas into a molten metal.

In any event, the scaffold is preferably bonded to the implant substrate by, for example, diffusion bonding.

After diffusion bonding, the finished implant may undergo further finishing and shaping, followed by sterilization and packaging.

DETAILED DESCRIPTION OF THE FIGURES

Figure 1:
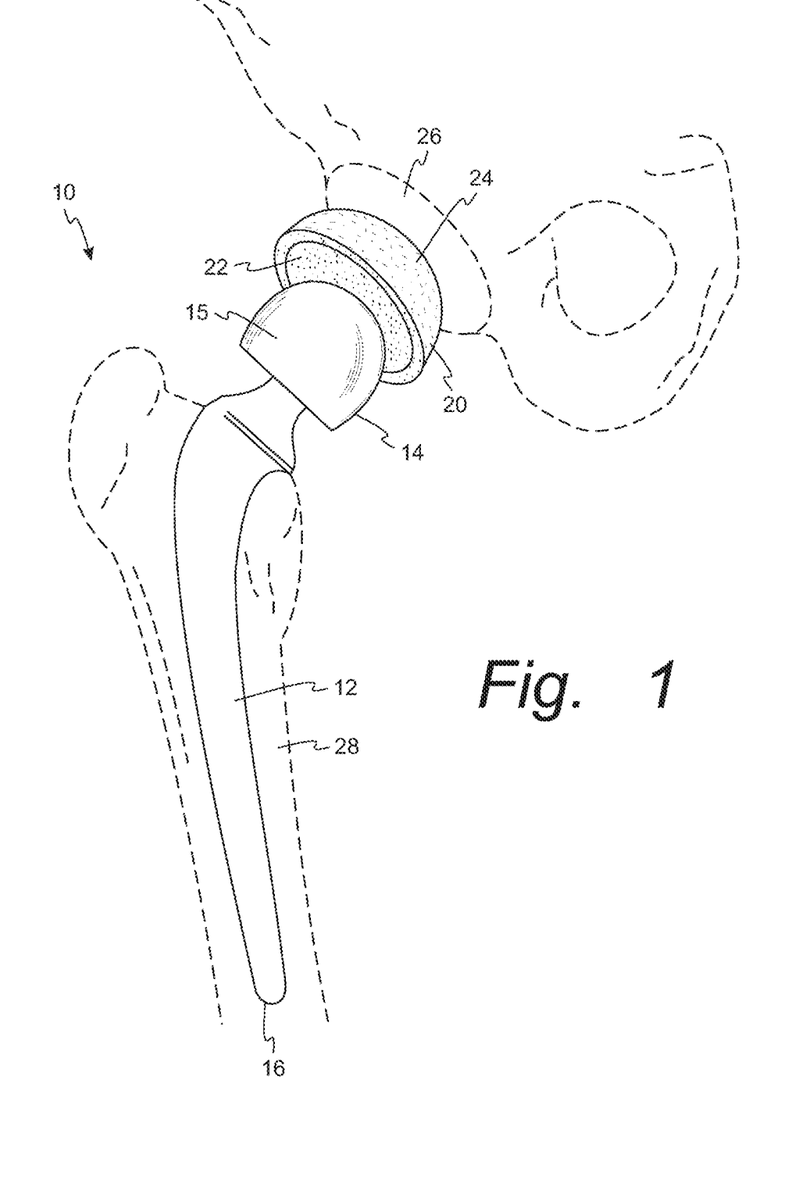
FIG. 1 is a perspective view of a hip implant system embodying the subject matter of the present disclosure.
Figures 2, 2A:
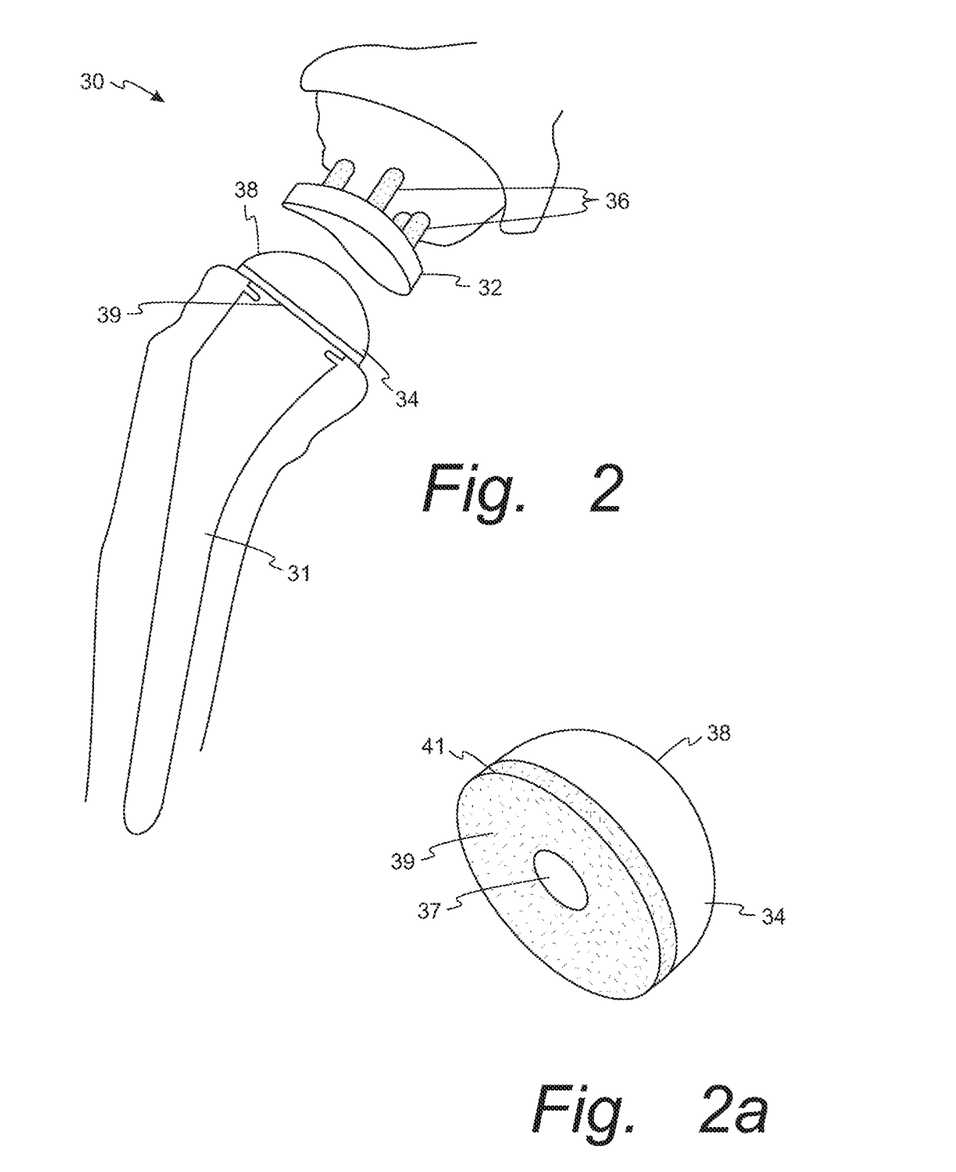
FIG. 2 is a perspective view of a shoulder implant system embodying the subject matter of the present disclosure.
FIG. 2a is an enlarged perspective view of the humeral head component of the implant system of FIG. 2.
Figure 3:
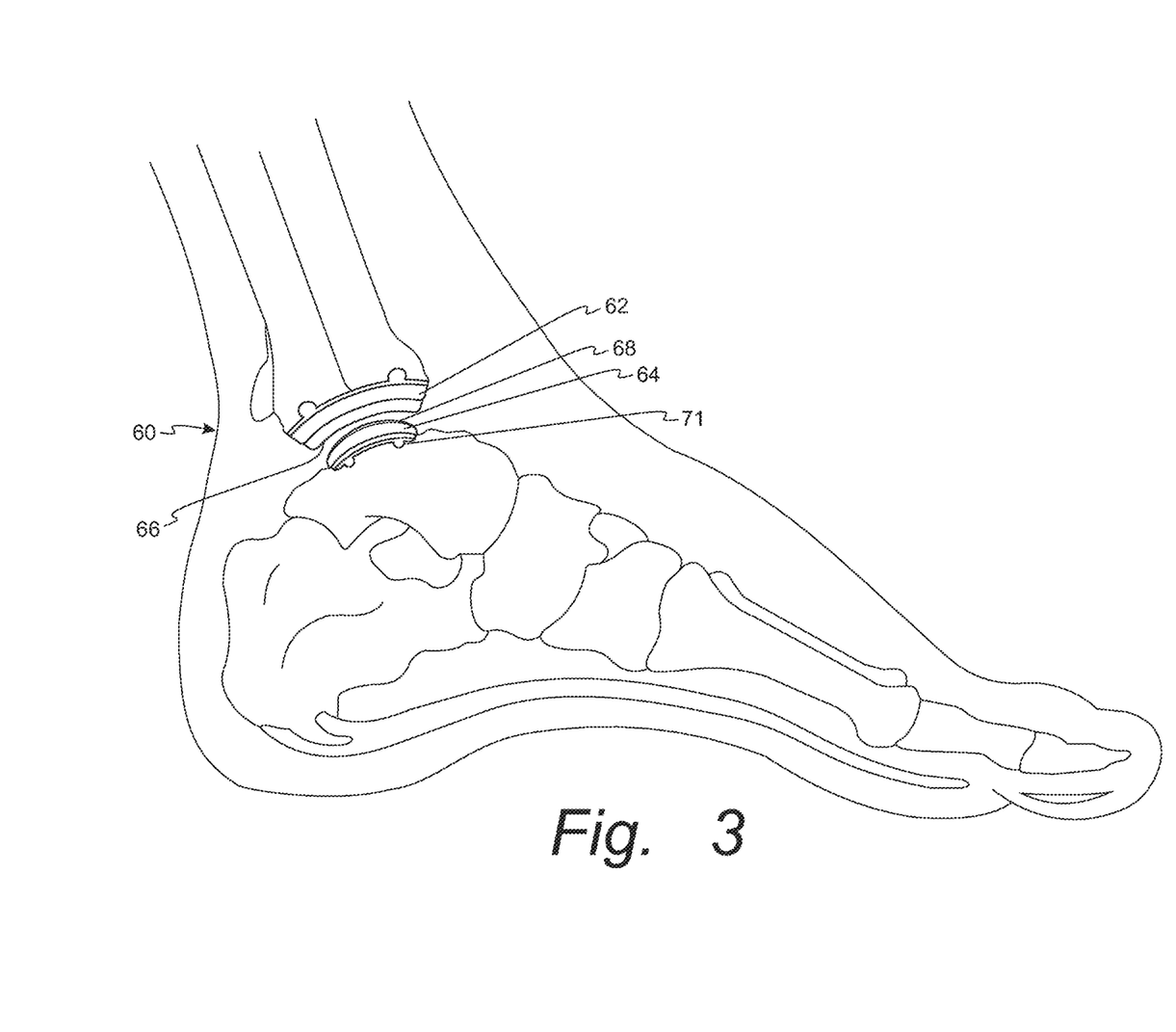
FIG. 3 is a perspective view of an ankle implant system embodying the subject matter of the present disclosure.
Figure 3A:
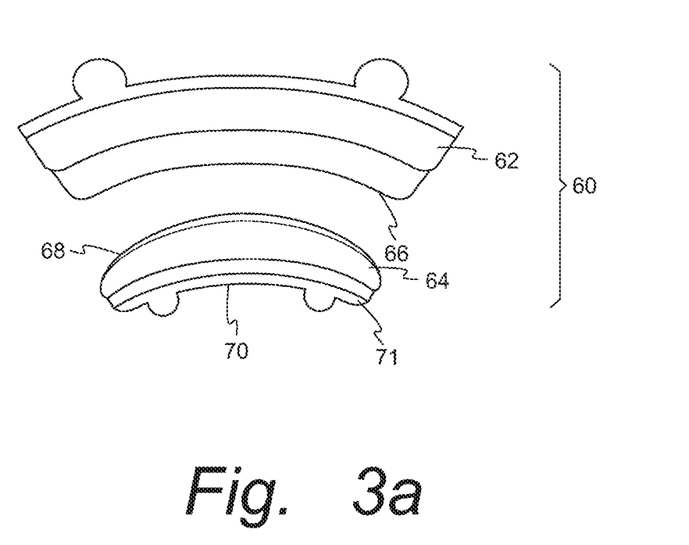
FIG. 3a is an enlarged perspective view of the ankle implant system of FIG. 3.

Shown in FIG. 1 is a hip implant system wherein at least one of the components, i.e., acetabular cup 20, is made in accordance with the methods described herein. FIGS. 2 and 2a show a shoulder implant system that likewise embodies implants and methods of the present disclosure. FIGS. 3 and 3a show an ankle implant system that embodies implants and methods also described herein. While these exemplary embodiments are described in greater detail below, it will be understood that the methods and systems set forth herein are not limited to hip, shoulder, or ankle implants. The subject matter of the present disclosure may find application in any orthopedic implant or implant systems where it is desirable to provide a low-friction, preferably ceramic, articulating surface and an osseointegrative layer or surface in a monoblock implant construct. Thus, the methods, implants and implant systems described herein may also find application to knee, finger, wrist, toe, spine, elbow implants and the like, as well as dental implants.

Turning more particularly to FIG. 1, hip implant system 10 includes a femoral stem 12 having a proximal end 14 and a distal end 16. As shown in FIG. 1, proximal end 14 terminates in a femoral head 15, which articulates against a corresponding surface of acetabular cup 20. As further shown in FIG. 1, during surgical implantation, femoral stem 12 is inserted into the reamed canal of femur 28.

Acetabular cup 20, shown in FIG. 1, is implanted within socket 26 of the patient's acetabulum. Acetabular cup 20 is provided in the shape of a semi-hemispherical component providing a cavity that also defines inner surface 22 and, more particularly, the inner surface against which femoral head 15 articulates. As shown in FIG. 1, the cavity (i.e., inner surface 22) is concavely-shaped so as to receive femoral head 15 and allow for a range of motion comparable to that provided by a normal, healthy hip joint. Outer surface 24 is typically rounded or provided with chamfers, and provides the bone-contacting surface of cup 20.

In accordance with the present disclosure, at least articulating surface 22 of cup 20 is made of a low-friction, non-metallic, non-polymeric material. Preferably, articulating surface 22 is made of a ceramic material that is suitable for use in biomedical applications. More typically, entire cup 20 is made substantially or even entirely of the low friction, non-metallic, non-polymeric material, such as ceramic with a selected surface (e.g., surface 24) of the ceramic cup modified to provide the bone-contacting layer as described in detail below.

The ceramic material selected must be suitable and approved for human use, i.e., biocompatible. Preferably, the ceramic material is likewise corrosion resistant, substantially wear resistant, and has a low coefficient of friction. The ceramic material should also have good mechanical strength. Examples of suitable ceramic materials include, but are not limited to, aluminum oxide, zirconium oxide, silicon nitride, zirconia-toughened alumina (ZTA) and alumina-toughened zirconia (ATZ).

As further shown in FIG. 1, implant (e.g., acetabular cup 20) includes outer surface 24 that has been adapted to allow for and promote osseointegration of the implant with the natural bone of the patient. In one embodiment, outer surface 24 preferably includes a porous metallic material selected to allow for and promote bone growth. Suitable materials include certain metallic materials based on, for example, titanium and tantalum. Certain metals or metal-containing materials are sufficiently porous or can be deposited in a way that creates a porous surface that allows for bone ingrowth. In a preferred embodiment, the metallic materials that can be used to provide the osseointegrative surface of implant 20 include metallic foams, such as titanium foam, tantalum foam, or stainless steel foam.

One example of suitable metallic foam is Trabecular Metal™. Trabecular Metal™ is a material used in orthopedic implants made by Zimmer, Inc., of Warsaw, Ind., and is described in, for example, U.S. Pat. No. 5,282,861, which is incorporated herein by reference. Trabecular Metal™ approximates the physical and mechanical properties of natural bone. It is highly porous and conducive to bone growth. Trabecular Metal™ has good corrosion resistance and is, of course, biocompatible. Trabecular Metal™ is formed by coating the surface of a pre-formed carbon foam with tantalum metal by, for example, chemical vapor deposition (CVD).

As previously noted, the methods and systems described above are not limited to a acetabular cups for hip implant systems. Other implant components and other implant systems may also utilize the methods and systems described herein.

For example, as shown in FIG. 2, the methods and systems of the present disclosure may also find application in a shoulder implant system 30. Shown in FIG. 2 are the glenoid component 32 and humeral component 31 of an orthopedic shoulder system 30. Humeral component 31 includes an elongated portion terminating in a humeral "head" 34 at its proximal end. Humeral head 34 includes at least an articulating or bearing surface 38 made of a low friction material such as ceramic. Preferably, the entire or at least substantially the entire humeral head component is made of the ceramic material. Surface 39 opposite the bearing surface 38 of the humeral head component provides the bone-contacting surface. More specifically, as in the hip system of FIG. 1, the surface 39 of humeral head 34 that is opposite the articulating surface 38 is modified to provide an osseointegrative surface. As further shown in FIG. 2a, the portion of humeral head component that serves as the osseointegrative surface 39 may be in the form of a disc 41 that is bonded to the under surface of ceramic humeral (head) 34 in the manner described in more detail below. Disc 41 may include an aperture 37 for receiving or otherwise accommodating the stem (not shown) of the elongated portion of humeral component 31. In another embodiment, the portion of humeral head 34 intended for bone contact may be a ring or may be provided in any shape or structure that bonds to the treated undersurface of humeral head 34. As described in more detail below, disc 41 or ring may be provided as a separately formed scaffold that is bonded to the bone contacting surface of humeral head 34 that faces the bone of the patient.

In yet another example of providing a monoblock implant made substantially of ceramic and including an osseointegrative surface, FIGS. 3 and 3a show an implant system for the ankle. As shown in FIGS. 3 and 3a, an ankle implant system 60 includes a tibial component 62 and a talar component 64. Tibial component 62 will typically include a polymeric bearing surface 66 against which surface 68 of talar component 64 articulates. Surface 68 of talar component 64, or substantially all of talar component 62, may be made of a low friction material, such as ceramic and, more specifically, the ceramic materials described above in connection with acetabular and humeral monoblock components.

Referring to FIG. 3a, the surface opposite articulating surface 68 of talar component 64 is the osseointegrative surface 70 which is adapted to promote bone growth. As in the examples described above, surface 70 may be provided as a scaffold 71 that is bonded to the mostly or entirely ceramic talar component 64. The osseointegrative materials previously described in connection with other monoblock implants are suitable for use with the talar component 64 described above and shown in FIGS. 3 and 3a.

Figure 10:
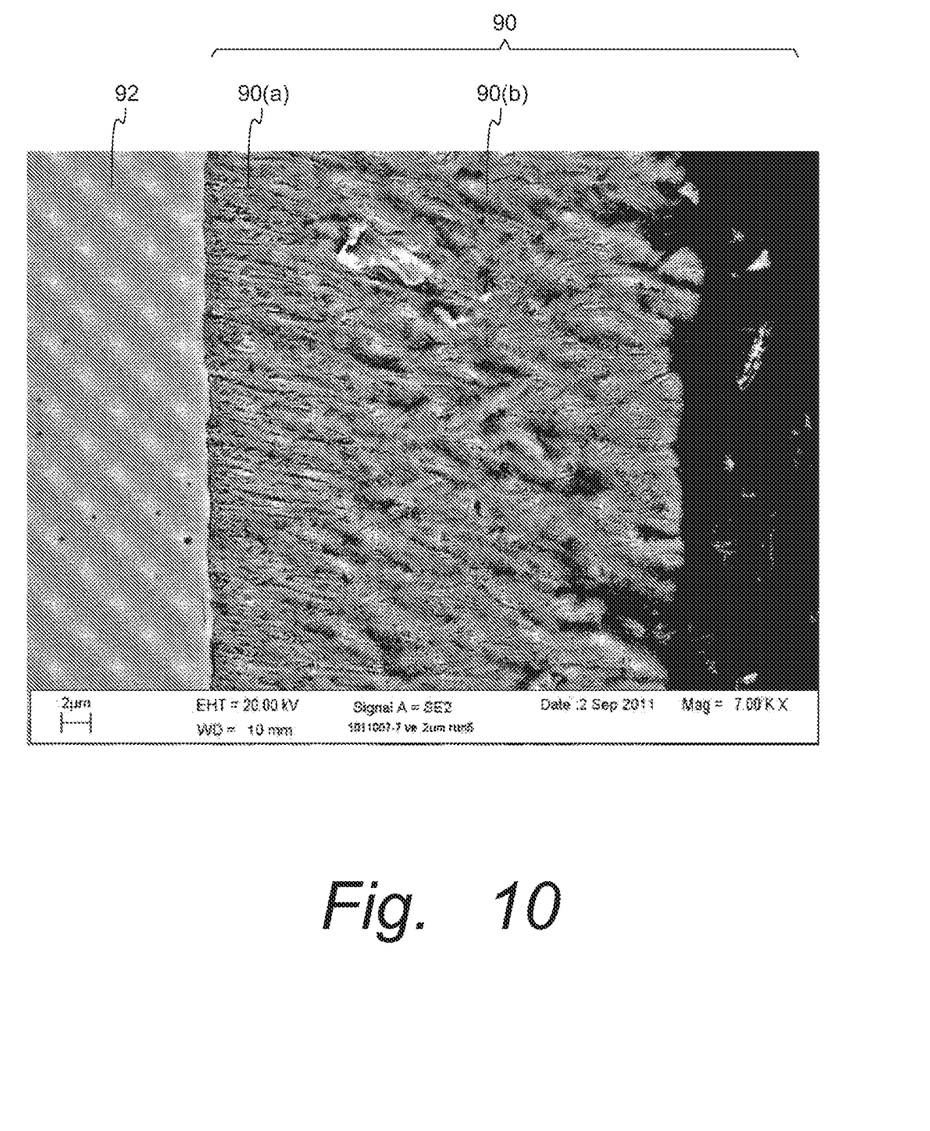
FIG. 10 is a SEM micrograph showing, in cross-section, a titanium layer coated onto a ceramic substrate.

Thus, in its most general form, a monoblock ceramic-based implant of the present disclosure includes a ceramic articulating surface and an integrally bonded bone-contacting surface that allows for and promotes bone-in growth bonded thereto. However, as will become apparent from the following discussion of the method of making such implants, the monoblock implant and the starting pre-form is preferably subjected to one or more treatments and/or depositions of other materials that allow for effective attachment of the bone-contacting material to the pre-form(ed) substrate. Such treatments and/or depositions may or may not be clearly visible to the naked eye upon inspection of a finished implant. However, for purposes of clarity and understanding, they are shown in the FIGS. 4-7 and discussed in greater detail below. In addition, FIG. 10 is a scanning electron microscope (SEM) micrograph that shows bonding of a metal layer to a ceramic substrate in accordance with the methods described herein.

Turning now to the method of making monoblock implants of the present disclosure, such orthopedic implants can be made in several different ways. FIGS. 4-7 depict the sequence of steps in one such exemplary method. The method of making a ceramic monoblock described below and depicted in FIGS. 4-7 are presented in the context of an acetabular cup. However, it will be appreciated that the discussion that follows is also generally applicable to the method of making any monoblock implants including the humeral head 34 of FIGS. 2 and 2a and talar component 64 of FIGS. 3 and 3a described above. Thus, it will be understood that humeral head 34 and talar component 64 may be provided as ceramic pre-forms with a surface that is modified and onto which a suitable scaffold may be bonded. The discussion that follows also applies to other ceramic-based monoblock implants, such as a glenoid component of a shoulder implant system, metacarpalphalangeal (MCP) joints and the like, as well as dental implants.

Figure 4A:
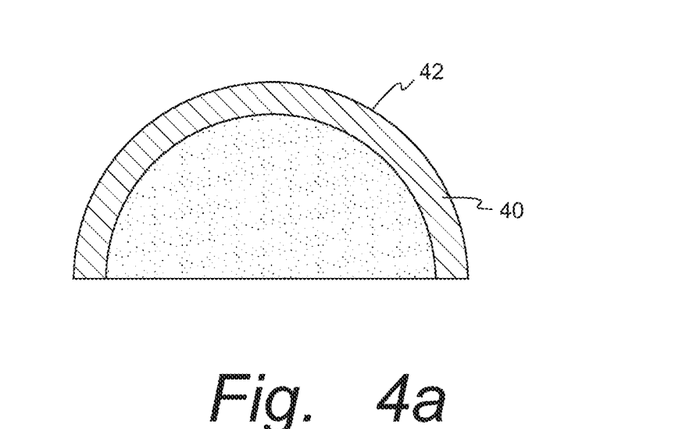
FIG. 4a is a cross-sectional view of a pre-formed ceramic substrate for use in the method of making a monoblock implant in accordance with the present disclosure.

As shown in FIG. 4a, a ceramic substrate 40 is provided. Substrate 40 (shown in cross-section) includes an outer bone interfacing surface 42 and an inner bearing or articulating surface 44. Ceramic substrate 40 may be pre-formed in the shape of the desired orthopedic implant. For exemplary purposes, and without limitation, a pre-form in the shape of an acetabular cup, is shown in FIG. 4a, although as noted above, the pre-form may be in the shape of humeral head 34 (FIG. 2), talar component 64 (FIG. 3), or in any other desired shape for the implant. The substrate or pre-form may be made substantially of a ceramic material, such as aluminum oxide, zirconium oxide, or silicon nitride.

Figure 4B:
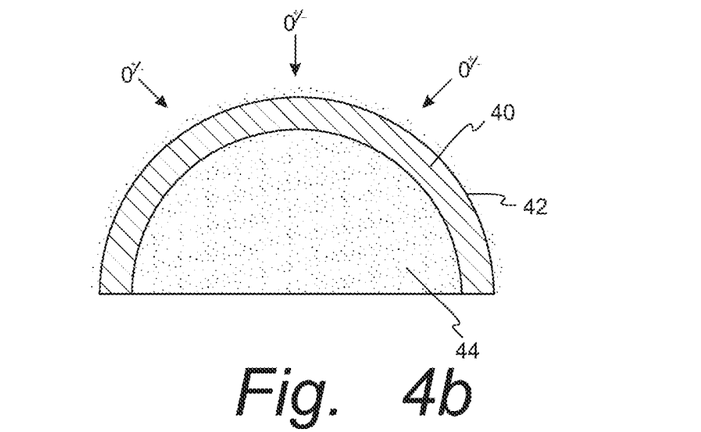
FIG. 4b is a cross-sectional view of the pre-formed substrate of FIG. 4a undergoing an oxygen treatment to provide an oxygen rich surface.

Bone interfacing surface 42 of ceramic pre-form 40 is preferably activated to provide a surface for bonding materials adapted for osseointegration, as well as for intermediate coatings, layers and depositions that allow for integral attachment of the bone ingrowth promoting material to the ceramic substrate. For example, as shown in FIG. 4b, outer surface 42 may be activated or otherwise treated to provide an oxygen rich surface. Inasmuch as ceramic by itself does not provide the desired osseointegrative and attachment properties, treating or activating the ceramic outer surface 42 to provide an oxygen-rich surface allows for subsequent bonding of the osseointegrative materials described below.

An oxygen rich surface 42 may be provided in several different ways. For example, an oxygen rich outer surface 42 may be provided by subjecting the ceramic surface to oxygen plasma etching.

Another method for imparting the oxygen rich properties to the ceramic outer surface 42 is by multiple energy oxygen ion implantation. Ion beam implantation is a process that changes the physical and electronic properties of a material by forcibly embedding different types of ions onto the material. In general, the ion implanter includes an ionization chamber where ions are created and an accelerator where they are boosted up to speeds high enough to penetrate the target material to the desired depth. In accordance with the present method, the ions are oxygen ions that are embedded onto the ceramic outer surface 42. The oxygen ion implantation method described herein includes applying energy of approximately 200-800 KeV.

Once the ceramic surface has been treated to provide an oxygen rich activated surface, such activated surface 42 may be further treated by depositing one or more metallic materials onto the surface. The deposited metallic materials (which can be provided as a paint, coating or sheet metal) are selected such that the metal firmly bonds to the activated oxygen rich surface of the ceramic pre-form 40 and likewise bonds to a final osseointegrative, i.e., bone-contacting surface of the implant. For example, where the osseointegrative bone-contacting surface includes the previously described metallic foams, materials that may bond to such foams and the ceramic substrate include titanium, titanium-aluminum-vanadium or zirconium, and/or alloys of one or more of the above.

Figure 5:
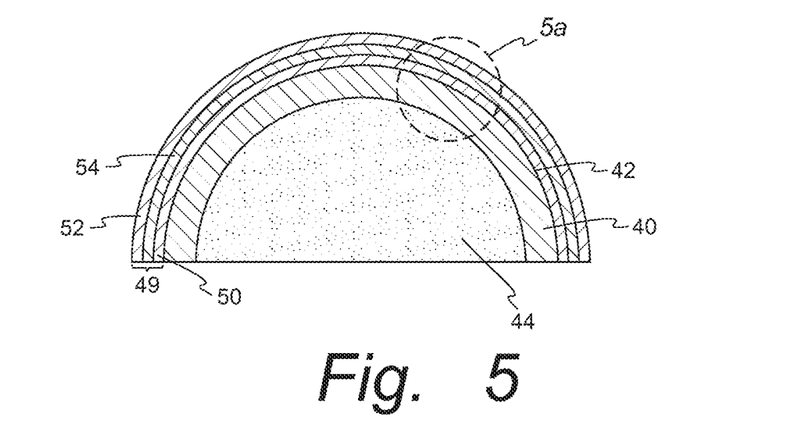
FIG. 5 is a cross-sectional view of the substrate of FIG. 4b including a deposited multi-layer of metal on the oxygen rich surface of the substrate.
Figure 5A:
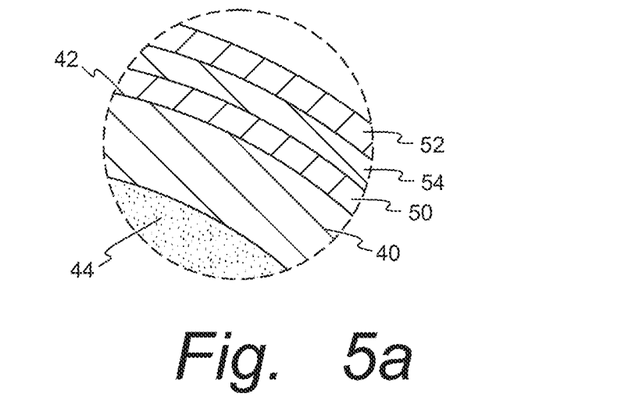
FIG. 5a is an enlarged cross-sectional view of the deposited multi-layer of metal of FIG. 5.

In one embodiment, the activated ceramic surface is preferably treated with multiple layers or depositions of a metal or metallic-based material as generally depicted in FIGS. 5 and 5a. As shown in FIGS. 5 and 5a, multiple layers or coatings of selected metallic materials are deposited onto the oxygen rich surface 42 of the ceramic implant pre-form 40. As shown in FIG. 5, and in greater detail in FIG. 5a, the multiple materials may include three deposited layers or coatings of selected metallic materials.

In one embodiment, layers or coatings 50 and 52 may be titanium layers, while intermediate layer 54 may be any material that can serve as a thermal expansion compensator which is described in greater detail below. Typically, each of the layers 50, 52 and 54 will be applied sequentially and the combined multi-layered construct 49 (FIGS. 6-7) may have a thickness of typically between 3-5 µm and up to about 1 mm. Of course, the thickness of the multi-layered construct will depend, in part, on the type and size of implant. Layers 50, 52 and 54 may be applied to surface 42 by a variety of techniques including, but not limited to, electron beam evaporation, sputter deposition, plasma spray, spray painting of dispersed powder suspensions, and other comparable processes that will be known to those of skill in the art.

FIG. 10 is a SEM micrograph of a Ti layer 90 bonded to a ceramic (zirconia) substrate 92. In one embodiment, the thickness of the overall titanium (or other metal) layer may be between about 15 µm and 40 µm. In the embodiment of FIG. 10, the thickness of the titanium layer is approximately 35 µm. As further shown in FIG. 10, the titanium layer may include a coarse region 90(*a*) adjacent to the ceramic substrate and a fine(r) region 90(*b*) spaced from the ceramic substrate. In the example of FIG. 10, the coarse region 90(*a*) may have a thickness of about 5 µm and the fine(r) region may have a thickness of about 30 µm. It is believed that a less coarse, finer layer of the metal may aid in the bonding of the scaffold to the substrate, as discussed below.

Figure 6:
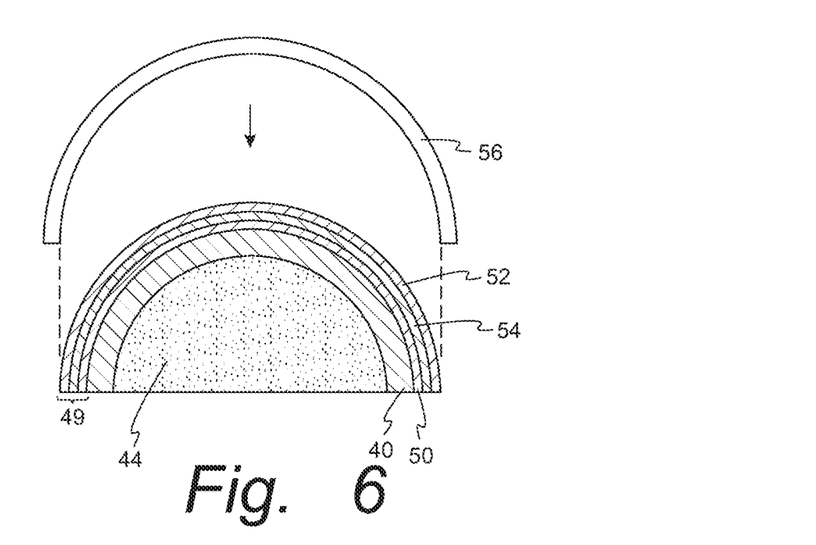
FIG. 6 is a cross-sectional view of the implant of FIG. 5 and a pre-formed metallic scaffold being applied thereon.

As shown in FIG. 6, implant 40 may be further modified to include an outer bone-contacting, osseointegrative surface. As discussed above, the material selected for the osseointegrative surface should likewise be a material suitable for bonding to the titanium (or other metal) layer 52 previously deposited onto the modified substrate 42.

As shown in FIG. 6, the outer bone-contacting surface may be provided as a pre-formed scaffold 56 that is attached to the modified surface 52 of implant 40. Scaffold 56 may be provided in any shape that conforms to the desired surface of the selected implant component (e.g., humeral head, talar component, etc.). Scaffold 56 may be substantially made of the previously described metallic foams, such as titanium foam, or the tantalum foam including, but not limited to Trabecular Metal™. Scaffold 56 may be made by casting. Alternatively, scaffold 56 may be made by providing a carbon foam in a predetermined shape and depositing the desired (metal) material onto the foam. In yet another alternative, scaffold may be made by bubbling gas into a molten metal.

In any event, scaffold 56 is preferably bonded to implant substrate 40 by, for example, diffusion bonding. Diffusion bonding of scaffold 56 to multi-layer 49 may be carried out at temperatures higher than about 800° C. and under torques of at least 10 Nm. As discussed above in connection with FIGS. 5 and 5a, titanium layer 52 will bond to a metallic foam of scaffold 56 when subjected to diffusion bonding. Likewise, titanium layer 50 will diffusion bond to the activated surface 42 of ceramic implant substrate 40. However, inasmuch as ceramic and titanium may undergo thermal expansion at different rates, thereby creating the potential for interfacial residual stress, intermediate layer 54 may be provided as a thermal expansion compensator. A thermal expansion compensator 54 compensates (i.e., by absorbing) the stresses caused by differences in the thermal expansion of varying materials. The thermal expansion compensator may be any material that is compatible with the surrounding layers or coatings. In a preferred embodiment where layers 50 and 52 are made of titanium, intermediate layer 54 is preferably made of molybdenum or other similar material. Zirconium may also be used as the thermal expansion compensator. Preferably, however, the multi-layer construct 49 is a titanium/molybdenum/titanium intermediate layer deposited between outer surface 42 of ceramic substrate 40 and scaffold 56.

The finished implant 58 (FIG. 7) thus provides a monoblock structure wherein its component portions and layers are integrally bonded together without the use of any locking mechanisms in a high-strength bond. For example, scaffolds of the type described above and made of porous metal such as Trabecular Metal™ and bonded to a ceramic substrate with a titanium/molybdenum/titanium interlayer therebetween having a bond strength that exceeds 20 MPa and will typically exceed 30 and even 40 MPa. In one specific embodiment, an acetabular cup made of alumina-zirconia (ceramic) with a Trabecular Metal™ scaffold bonded with a titanium/molybdenum/titanium interlayer having a thickness of about 2 mm, had a bond strength of about 43 MPa, as measured per ASTM F1147. The monoblock implant provides a low-friction ceramic bearing surface that allows the substantially ceramic implant to be affixed to natural bone and promotes osseointegration with such bone.

Figure 7:
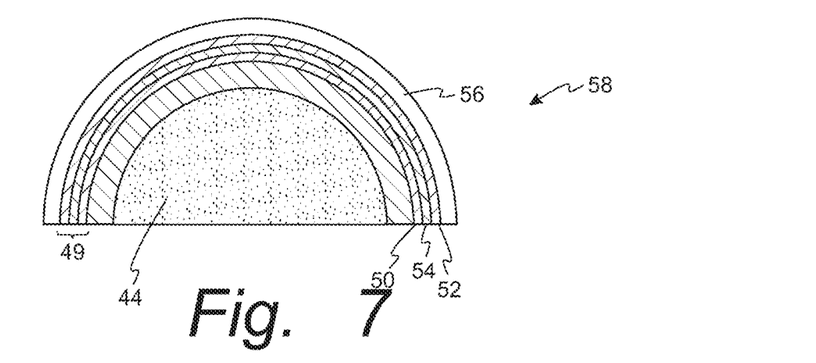
FIG. 7 is a cross-sectional view of the implant made in accordance with the present disclosure showing the scaffold of FIG. 6 bonded to the modified outer surface of the substrate.

After diffusion bonding, the finished implant 58 may undergo further finishing and shaping, followed by sterilization and packaging.

Figure 8:
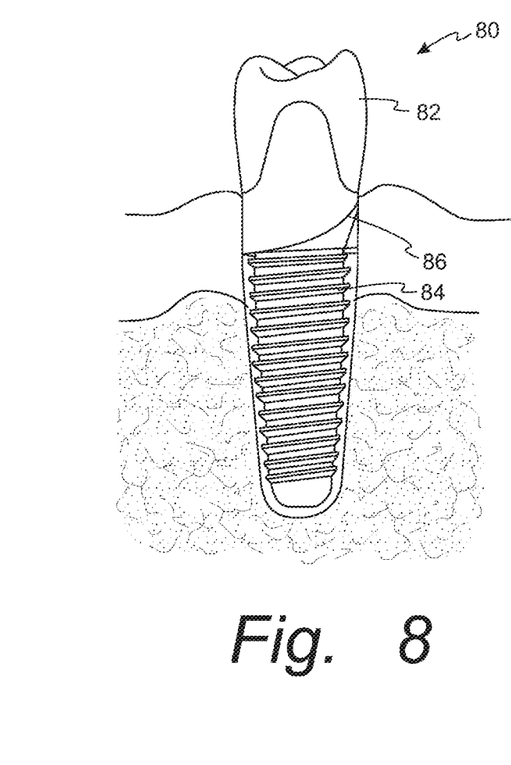
FIG. 8 is a plan view of a dental implant embodying the subject matter of the present disclosure.
Figure 9:
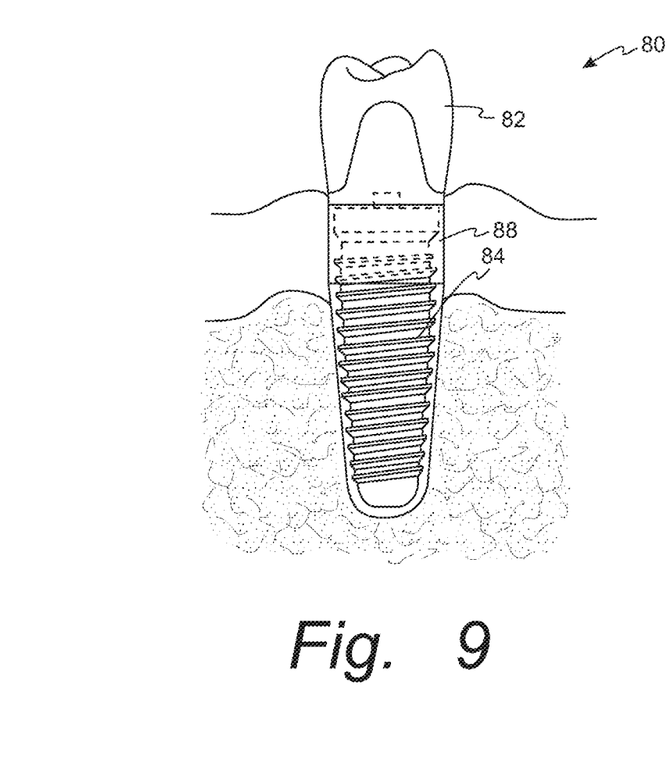
FIG. 9 is a plan view of an alternative dental implant embodying the subject matter of the present disclosure.

In a further aspect, the methods or devices described herein may find application to or be embodied in dental implants, such as dental crowns. Shown in FIGS. 8 and 9 are embodiments of a dental crown 80 made in accordance with the present disclosure. Crown 80 includes cap 82 that is preferably made of ceramic. Cap 82 may serve as the preform that is treated and to which a metallic member 84 is attached. Specifically, underside 86 of cap 82 may be treated to provide an oxygen rich surface that receives a metallic multi-layered film or a coating in the manner described above. Metallic member 84 is preferably provided in the form of a screw and is bonded to the underside 86 of cap 82 to provide a unitary (e.g., monoblock) dental crown. Screw 84 or other attachment member is preferably made of a metallic foam, such as Trabecular Metal™, to allow for bone ingrowth. Crown 80 may further include a central rod (not shown) to provide screw 84 with additional structural strength. The central rod may be made of stainless steel, titanium, cobalt-chrome or other suitable material.

In one embodiment, cap 82 may include a central aperture (not shown) through which a driver may be introduced to screw or otherwise attach screw or other member to the bone. Once dental crown 80 has been secured, the aperture is preferably filled with a composite material. Alternatively, as shown in FIG. 9, cap 82 may include skirt 88 that overhangs screw 84. Skirt 88, which may be bonded to cap 82 in accordance with the methods previously described, is preferably made of a metallic foam such as Trabecular Metal™ to allow for bone or soft tissue attachment. In this embodiment, as skirt 88 provides the area adapted bone or tissue attachment, screw 84 may but need not be made of a metallic foam. Alternatively, cap 82 with skirt 88 may be bonded to screw 84 through epoxy or other suitable adhesives.

It will be understood that the embodiments above are illustrative of some of the applications of the principles of the present subject matter. Numerous modifications may be made by those skilled in the art without the departing from the spirit and scope of the claimed subject matter, including those combinations of features that are individually disclosed or claimed herein. For these reasons, the scope hereof is not limited to the above description.

That which is claimed:

1. A monoblock orthopedic implant, comprising:
   a ceramic substrate comprising an inner bearing surface and a treated outer surface;
   a metallic scaffold adapted for osseointegration; and
   a multi-layer construct positioned between the ceramic substrate and the metallic scaffold, the multi-layer construct comprising:
   an inner layer formed of a first material, the inner layer positioned on the treated outer surface, wherein the first material is a metallic material;
   an intermediate layer formed of a second material; and
   an outer layer formed of a third material, wherein the second material is different from the first material and the third material.

2. The monoblock orthopedic implant of claim 1, wherein the metallic scaffold comprises a metal foam.

3. The monoblock orthopedic implant of claim 2, wherein the metal foam is selected from the group consisting essentially of a titanium foam, a tantalum foam, and a stainless steel foam.

4. The monoblock orthopedic implant of claim 1, wherein the ceramic substrate is selected from the group consisting essentially of aluminum oxide and zirconia oxide.

5. The monoblock orthopedic implant of claim 1, wherein one or more of the intermediate layer and the outer layer of the multi-layer construct are of a metallic material.

6. The monoblock orthopedic implant of claim 1, wherein the multi-layer construct comprises a surface adapted for bonding to the ceramic substrate and a surface adapted for bonding to the metallic scaffold.

7. The monoblock orthopedic implant of claim 1, wherein the inner layer includes the surface adapted for bonding to the ceramic substrate and the outer layer includes the surface adapted for bonding to the metallic scaffold.

8. The monoblock orthopedic implant of claim 1, wherein the intermediate layer is adapted to accommodate temperature expansion differences between the ceramic substrate and the other layers.

9. The monoblock orthopedic implant of claim 1, wherein the inner layer comprises titanium, the intermediate layer comprises molybdenum, and the outer layer comprises titanium.

10. The monoblock orthopedic implant of claim 1, wherein the first material and the third material are the same.

* * * * *